United States Patent
Taoka et al.

(10) Patent No.: US 7,573,979 B2
(45) Date of Patent: Aug. 11, 2009

(54) X-RAY IMAGING DEVICE

(75) Inventors: Akira Taoka, Hamamatsu (JP); Kazuhisa Miyaguchi, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 11/885,767

(22) PCT Filed: Mar. 7, 2006

(86) PCT No.: PCT/JP2006/004326

§ 371 (c)(1),
(2), (4) Date: Apr. 29, 2008

(87) PCT Pub. No.: WO2006/095714

PCT Pub. Date: Sep. 14, 2006

(65) Prior Publication Data

US 2008/0198969 A1    Aug. 21, 2008

(30) Foreign Application Priority Data

Mar. 8, 2005    (JP)    .............................. 2005-064343

(51) Int. Cl.
*H05G 1/64*    (2006.01)
(52) U.S. Cl. ..................... 378/98.8; 378/116
(58) Field of Classification Search ............... 378/98.8, 378/114, 115, 116, 191, 98.2
See application file for complete search history.

(56) References Cited

U.S. PATENT DOCUMENTS

| 6,149,300 | A | 11/2000 | Greenway et al. | |
| 6,185,274 | B1* | 2/2001 | Kinno et al. ................ | 378/98.8 |
| 6,977,988 | B2* | 12/2005 | Niwa ............................ | 378/95 |
| 2002/0186813 | A1* | 12/2002 | Tamura et al. ............. | 378/98.8 |
| 2007/0297567 | A1* | 12/2007 | Takenaka et al. ........... | 378/98.2 |

FOREIGN PATENT DOCUMENTS

| EP | 0 757 474 | 2/1997 |
| JP | 11-502055 | 2/1999 |
| JP | 11-188033 | 7/1999 |
| JP | 3335350 | 8/2002 |
| WO | WO 92/22188 | 12/1992 |
| WO | 03/094733 | 11/2003 |

\* cited by examiner

*Primary Examiner*—Hoon Song
(74) *Attorney, Agent, or Firm*—Drinker Biddle & Reath LLP

(57) ABSTRACT

When a signal S2 with a pulse width corresponding to an entire X-ray irradiation period is input, a pulse P3 (signal S5) with a predetermined pulse width is output at an input timing of the signal S2, and when a new signal S2 is input during output of the pulse P3, the pulse P3, being output, is extendingly output further for the above pulse width from the input timing of the signal S2. Then in a state in which either or both of the signal S2 and the pulse P3 are being input, a pulse P4 (signal S6), with a pulse width corresponding to a period of the input, is output at a start timing of the input period, and when the pulse P4 is input, the imaging unit 7 is controlled to start imaging based on a start timing of the pulse P4. An X-ray imaging apparatus that can appropriately detect an imaging start timing and can perform taking of a good X-ray image while preventing malfunctions due to noise is thereby realized.

3 Claims, 6 Drawing Sheets

(a)

(b)

X-RAY IMAGING DEVICE

TECHNICAL FIELD

The present invention relates to an X-ray imaging apparatus for taking X-ray images.

BACKGROUND ART

Recently, various X-ray imaging systems, which use a CCD (charge coupled device) to take an X-ray image of teeth, etc., of a subject, have been proposed (see, for example, Patent Documents 1 and 2, indicated below). Such an X-ray imaging system has an X-ray irradiating apparatus that irradiates X-rays and an X-ray imaging apparatus that takes an X-ray image obtained by the X-ray irradiation. The X-ray imaging apparatus has an imaging unit, having a CCD for taking the X-ray image, an X-ray detecting unit, for detecting whether or not X-ray irradiation is being performed, and a controlling unit, for drive control of the imaging unit and the X-ray detecting unit.

Here, the X-ray detecting unit is a photodiode, etc., that photoelectrically converts the irradiated X-rays and outputs an X-ray detection signal. The controlling unit detects, on the basis of the X-ray detection signal output from the X-ray detecting unit, a start timing (or, further, an end timing) of an entire X-ray irradiation period for each single time of X-ray imaging (referred to hereinafter simply as the "entire X-ray irradiation period") and, based on the detected timing, generates a trigger that indicates an imaging start timing (or, further, an imaging end timing). Based on this trigger, the controlling unit performs drive control of the CCD to perform X-ray imaging.

Patent Document 1: Japanese Translation of PCT International Application No. H11-502055

Patent Document 2: Japanese Patent No. 3335350

DISCLOSURE OF THE INVENTION

Problems to be Solved by the Invention

Because the above-mentioned conventional X-ray irradiating apparatus is driven using a voltage, obtained by half-wave rectification of an AC power supply (commercial AC power supply), as a high voltage, the X-ray irradiation is cyclic in accordance with the half-wave rectified voltage waveform of the AC power supply voltage. The conventional X-ray imaging apparatus is thus arranged to be able to appropriately detect the start timing and the end timing of the entire X-ray irradiation period in accordance with such cyclic X-ray irradiation.

That is, with the conventional X-ray imaging apparatus, when the X-ray detection signal is output from the X-ray detecting unit, a pulse, with a specific pulse width that has been set in advance (a pulse width longer than an X-ray irradiation period of a single cycle), is output at the output timing of the X-ray detection signal. Although when the X-ray detection signal corresponding to a single cycle of X-ray irradiation is output from the X-ray detecting unit, just one pulse with the above-mentioned pulse width is output, when during the output of this pulse, the X-ray detection signal corresponding to the next single cycle of X-ray irradiation is output from the X-ray detecting unit, the currently output pulse is output extendedly with the pulse width being extended, by the length of the above-mentioned pulse width, from the input timing of the new detection signal.

Thus, with the conventional X-ray imaging apparatus, when cyclic X-ray irradiation is performed in accordance with a half-wave rectified waveform of an AC power supply voltage, pulses are successively output in synchronization with the X-ray irradiation cycles over the entire X-ray irradiation period and because the pulse width of each pulse is longer than the X-ray irradiation cycle width and a new pulse, corresponding to the next single cycle, is input during the output of each pulse, a single pulse, having a pulse width corresponding to the entire X-ray irradiation period, is consequently output from the X-ray imaging apparatus. By using the start timing and the end timing of the pulse with the pulse width corresponding to the entire X-ray irradiation period, the imaging start timing and the imaging end timing of X-ray imaging can be detected.

A conventional X-ray imaging apparatus such as that described above has a malfunction prevention function for preventing erroneous detection of the imaging start timing based on a single isolated signal due to electrical noise. That is, the conventional X-ray imaging apparatus detects the timing, at which a predetermined period (a period slightly longer than the above-mentioned specific pulse width) elapses from the output of a signal (the X-ray detection signal, etc.) from the X-ray detecting unit (a timing at which a malfunction prevention timer expires), as the imaging start timing. In this case, although the pulse with the above-mentioned specific pulse width is output according to the signal output from the X-ray detecting unit, settings are made so that if this pulse is already extinguished at the timing of elapse, detection of the above-mentioned imaging start timing is not performed. For example, if a signal output from the X-ray detecting unit is due to noise (a single isolated signal), the pulse will already be extinguished at the point of the timing of expiration of the malfunction prevention timer. Erroneous detection of the imaging start timing based on a pulse output due to such noise is thus made less likely to occur.

Meanwhile, with the recent development of medical care, there has been an increasing demand for X-ray irradiating apparatuses that perform DC irradiation using a complete DC voltage obtained from an AC power supply by a high-frequency inverter method instead of AC irradiation by half-wave rectification of an AC power supply. X-ray irradiation by such an X-ray irradiating apparatus that performs DC irradiation is not cyclic as in the case of a conventional X-ray irradiating apparatus that performs AC irradiation but is stationary in accordance with the voltage waveform of the complete DC voltage obtained by the high-frequency inverter method. However, with the conventional X-ray imaging apparatus that operates in accordance with cyclic X-ray irradiation as described above, even if stationary X-ray irradiation is performed in accordance with the voltage waveform of the complete DC voltage obtained by the high-frequency inverter method, the imaging start timing cannot be detected accurately due to the action of the malfunction prevention function and the taking of a good X-ray image is thereby made difficult. That is, in the case of stationary X-ray irradiation, when a detection signal, having the form of a single pulse that spans the X-ray irradiation period, is input into the X-ray imaging apparatus, only a single pulse with the specific pulse width is generated at the X-ray imaging apparatus by this detection signal. Because this pulse becomes extinguished before expiration of the malfunction prevention timer, detection of the start timing of the entire X-ray irradiation period based on this pulse is difficult. Consequently, the detection of the imaging start timing is difficult. The development of an X-ray imaging apparatus that can detect the imaging start timing even with stationary X-ray irradiation, which is in accordance with a voltage waveform of a complete DC voltage obtained by a high-frequency inverter method, is thus desired.

An object of the present invention is to provide an X-ray imaging apparatus that can appropriately detect the imaging start timing and enable a good X-ray image to be taken while preventing malfunctions due to noise regardless of whether the X-ray irradiation is cyclic in accordance with a half-wave rectified waveform of an AC power supply voltage or is stationary in accordance with a voltage waveform of a complete DC voltage obtained by a high-frequency inverter method.

Means for Solving the Problems

An X-ray imaging apparatus according to the present invention includes: an imaging unit, taking an X-ray image obtained by X-ray irradiation; an X-ray detecting unit, outputting, when X-rays are irradiated, an X-ray detection signal over an irradiation period; a first pulse output unit, outputting, when the X-ray detection signal is input from the X-ray detecting unit, a first pulse with a preset pulse width at an input timing of the X-ray detection signal and, when a new X-ray detection signal is input from the X-ray detecting unit during output of the first pulse, extendingly outputting the first pulse, being output, further for a period corresponding to the pulse width from the input timing of the new X-ray detection signal; a second pulse output unit, outputting, in a state where one or both of the X-ray detection signal and the first pulse are being input, a second pulse, with a pulse width corresponding to a period of the input, at a start timing of the input period; and a controlling unit, controlling, when the second pulse is input, the imaging unit to start imaging based on a start timing of the second pulse.

With the present invention, when, for example, the X-ray irradiation within the entire X-ray irradiation period is stationary in accordance with a voltage waveform of a complete DC voltage obtained by a high-frequency inverter method, the X-ray detecting unit outputs a stationary detection signal over the entire X-ray irradiation period and the first pulse output unit outputs the first pulse of the preset pulse width in synchronization with the output start timing of the stationary detection signal, output from the X-ray detecting unit (that is, in synchronization with the start timing of the entire X-ray irradiation period). During the period in which one or both of the detection signal output from the X-ray detecting unit and the first pulse output from the first pulse output unit are being input, the second pulse output unit outputs the second pulse, with the pulse width corresponding to the input period, at the start timing of the input period.

Thus, when the stationary detection signal spanning the entire X-ray irradiation period is output from the X-ray detecting unit, the input period at the second pulse output unit corresponds to the entire X-ray irradiation period (the period during which the detection signal is output from the X-ray detecting unit), and the second pulse output unit outputs the second pulse with the pulse width corresponding to the entire X-ray irradiation period at the start timing of the entire X-ray irradiation period.

When, for example, an electrical noise is generated inside the X-ray imaging apparatus, a signal due to this noise (a single pulse with a short pulse width) is input from the X-ray detecting unit into the first and second pulse output units, respectively. In many such cases, the pulse width of the first pulse output from the first pulse output unit in accordance with the input of the signal due to the noise is longer than the signal width of the signal that is output from the X-ray detecting unit due to the noise. In this case, the input period at the second pulse output unit corresponds to the pulse width of the first pulse that is output from the first pulse output unit, and the second pulse output unit outputs the second pulse with the pulse width of the first pulse output from the first pulse output unit.

Thus, if the controlling unit is arranged so that when the second pulse is input from the second pulse output unit, the controlling unit outputs a trigger, indicating the imaging start timing of X-ray imaging, at a timing of elapse of a period slightly longer than the preset pulse width from the start timing of the second pulse, a malfunction, in which the trigger indicating the start of imaging is output erroneously due to noise, can be suppressed adequately and the imaging start timing for an X-ray image can be detected appropriately. Thus, in the case where the X-ray irradiation within the entire X-ray irradiation period is a stationary X-ray irradiation that is in accordance with the voltage waveform of the complete DC voltage obtained by the high-frequency inverter method, the imaging start timing for the X-ray image can be detected appropriately while preventing malfunctions due to noise.

In a case where the X-ray irradiation within the entire X-ray irradiation period is cyclic in accordance with a half-wave rectified waveform of an AC power supply voltage, the X-ray detecting unit outputs a cyclic detection signal over the entire X-ray irradiation period, and the first pulse output unit outputs the pulse with the preset pulse width in synchronization with an output start timing of each single cycle of the detection signal output from the X-ray detecting unit (the start timing of each single cycle of X-ray irradiation in the entire X-ray irradiation period). In this process, if the cycle width of X-ray irradiation in the entire X-ray irradiation period is shorter than the preset pulse width, the pulse width of the pulse output by the first pulse output unit is extended until it corresponds to the entire X-ray irradiation period. The first pulse output unit thus outputs the first pulse with a pulse width corresponding to the entire X-ray irradiation period at the start timing of the-entire X-ray irradiation period.

During the period in which one or both of the cyclic detection signal output from the X-ray detecting unit and the pulse output from the first pulse output unit are being input, the second pulse output unit outputs the second pulse, having the pulse width corresponding to the input period, at the start timing of the input period. In the case the cyclic detection signal over the entire X-ray irradiation period is output from the X-ray detecting unit, the input period of the second pulse output unit corresponds to the entire X-ray irradiation period (the period in which the detection signal is output from the X-ray detecting unit), and the second pulse output unit outputs a stationary second pulse with a pulse width corresponding to the entire X-ray irradiation period at the start timing of the entire X-ray irradiation period.

If the controlling unit is arranged so that when the second pulse is input from the second pulse output unit, the controlling unit outputs the trigger, indicating the imaging start timing of X-ray imaging, at a timing of elapse of a period slightly longer than the preset pulse width from the input timing of the second pulse, a malfunction, in which the trigger indicating the start of imaging is output erroneously due to noise, can be suppressed adequately and the imaging start timing for an X-ray image can be detected appropriately. Thus, even in the case where the X-ray irradiation within the entire X-ray irradiation period is a cyclic X-ray irradiation that is in accordance with the voltage waveform of the AC power supply voltage, the imaging start timing for the X-ray image can be detected accurately while preventing malfunctions due to noise.

By the above, the imaging start timing for an X-ray image can be detected appropriately while preventing malfunctions due to noise and a good X-ray image can be taken in all cases regardless of whether the X-ray irradiation within the entire X-ray irradiation period is cyclic or stationary.

EFFECTS OF THE INVENTION

By the present invention, a start timing of an imaging period can be extracted appropriately to enable a good X-ray image to be taken while preventing malfunctions due to noise regardless of whether the X-ray irradiation is cyclic in accordance with a half-wave rectified waveform of an AC power supply voltage or is stationary in accordance with a voltage waveform of a complete DC voltage obtained by a high-frequency inverter method.

DESCRIPTION OF THE SYMBOLS

1—X-ray irradiating apparatus, 2—X-ray imaging apparatus, 3—PC, 4—display, 5—optical image acquiring unit, 6—controlling unit, 7—imaging unit, 8—connecting unit, 9—trigger generating unit, 10—X-ray imaging system, 11—tube, 12—holding member, 61—signal processor, 62—trigger processor, 63—I/O controller, 64—A/D converter, 65—CCD driver, 71—scintillator, 72—CCD, 73—CCD controller, 81—connector, 90—X-ray detecting unit, 91—PD, 92—amplifier, 92$a$—I-V converting amplifier, 92$b$—gain amplifier, 93—trigger generator, 93$a$—comparator, 93$c$—time-constant-determining C, R connection, 93$d$—NOR circuit, 93$b$—monostable multivibrator, L1—signal cable, L11—detection signal line, L12—controlling signal line, L13—image signal line, L14—GND line, L2—signal cable.

BEST MODES FOR CARRYING OUT THE INVENTION

A preferred embodiment of an X-ray imaging apparatus according to the present invention shall now be described in detail with reference to the drawings. In the description of the drawings, elements that are the same shall be provided with the same symbols and overlapping description shall be omitted.

Figure 1:
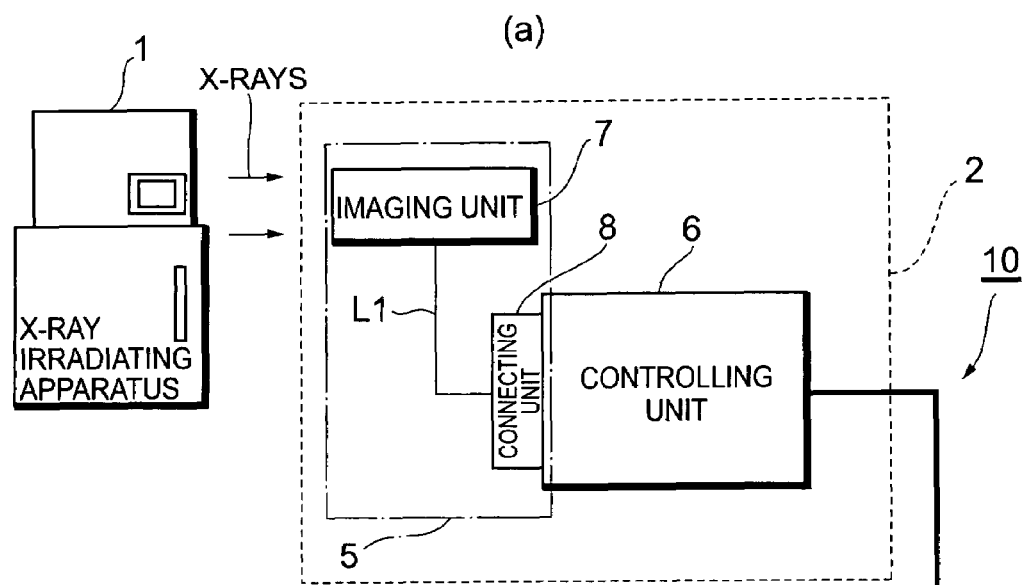
FIG. 1 shows a block diagram of an arrangement of an X-ray imaging system according to an embodiment.
Figure 1:
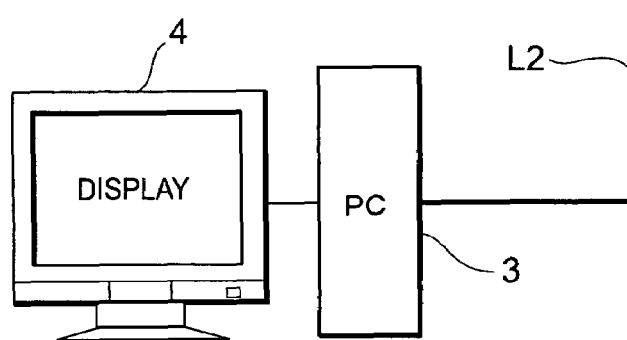
Figure 1:
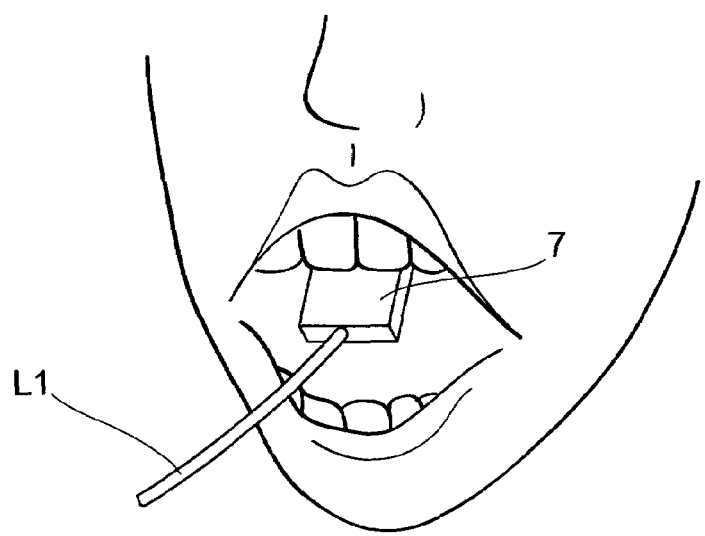

First, the arrangement of an X-ray imaging system 10 shall be described with reference to (a) in FIG. 1. The X-ray imaging system 10 is a medical-use X-ray imaging system for performing X-ray imaging of teeth, etc., of a subject. The X-ray imaging system 10 has an X-ray irradiating apparatus 1, an X-ray imaging apparatus 2, a PC (personal computer) 3, and a display 4.

The X-ray irradiating apparatus 1 is an X-ray irradiating apparatus for irradiating X-rays onto teeth, etc., and is arranged as a fixed installation type apparatus. In response to an X-ray irradiation start instruction, the X-ray irradiating apparatus 1 performs stationary X-ray irradiation in accordance with a voltage waveform of a complete DC voltage obtained by a high-frequency inverter method until an X-ray irradiation end instruction is input (or until expiration of an irradiation end timer). The X-ray irradiating apparatus 1 can also perform cyclic X-ray irradiation according to a half-wave rectified waveform of an AC power supply voltage.

The X-ray imaging apparatus 2 is an X-ray imaging apparatus for taking an X-ray image of teeth, etc., and has an optical image acquiring unit 5 and a controlling unit 6. The optical image acquiring unit 5 has an imaging unit 7 and a connecting unit 8 that are connected to each other via a signal cable L1.

The imaging unit 7 has a CCD 72 to be described below and takes an X-ray image of teeth, etc., by means of the CCD 72. The imaging unit 7 has dimensions and a shape that enable easy insertion into an oral cavity of a subject. An example of a state in which the imaging unit 7 is inserted in an oral cavity of a subject is shown in (b) in FIG. 1. The imaging unit 7 is inserted into an inner side of front teeth of an upper jaw of the subject, and the signal cable L1 extends from the imaging unit 7 to the exterior of the oral cavity.

The signal cable L1 has a shape and dimensions of a long, thin form and is a multicore cable with a diameter of approximately 3 mm, in which a dozen or so thin cables are bundled together. One or a plurality of cables of each of signal lines L11 to L13, that is, a detection signal line L11, a controlling signal line L12, and an image signal line L13 (see (a) in FIG. 2 and FIG. 3), all of which have excellent flexibility, are contained inside a tube 11, constituted of an outer sheath of a material of excellent flexibility, such as PVC or fluororesin, that can adequately lighten discomfort and pain inflicted on the subject in the state in which the imaging unit 7 is inserted in the oral cavity of the subject (see (b) in FIG. 1).

Figure 2:
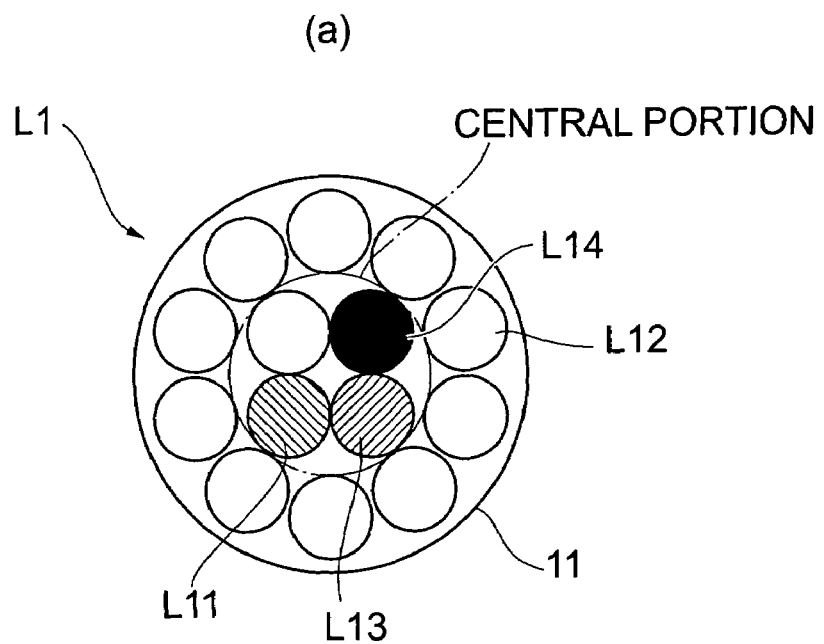
FIG. 2 shows schematic diagrams of a cross-sectional arrangement of an interior of a signal cable of the embodiment.
Figure 2:
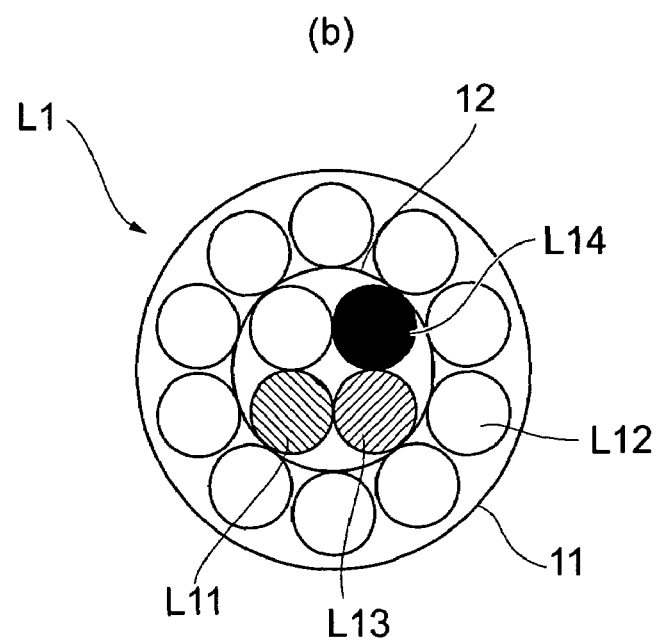

Here, as shown in (a) in FIG. 2, the signal cable L1 contains one each of the detection signal line L11 and the image signal line L13, eleven controlling signal lines L12, and a single GND (ground) line L14. The single detection signal line L11 and the single image signal line L13 are disposed, along with the single GND line L14 and a single controlling signal line L12, at the inner side of the signal cable L1, and ten controlling signal lines L12 are disposed at the outer side of these lines.

The details of the positions and the numbers of the signal lines L11 to L13 in the signal cable L1 are not restricted to those shown in (a) in FIG. 2 as long as these are as described above. For example, as shown in (b) in FIG. 2, the signal cable L1 may have a holding member 12, extending in a longitudinal direction of the tube 11, at the inner side of the tube 11, one each of the detection signal line L11, controlling signal line L12, image signal line L13, and GND line L14 may be positioned at the inner side of the holding member 12, and ten controlling signal lines L12 may be positioned at the outer side of the holding member 12. In this case, the holding member 12 is formed of paper or other material of excellent flexibility as is the tube 11. The holding member 12 may also be an arrangement, with which the detection signal line L11, controlling signal line L12, image signal line L13, and GND line L14 are bundled together by a tape-like member.

The controlling unit 6 is connected via a signal cable L2 to the PC 3. The controlling unit 6 controls the optical image acquiring unit 5 (in particular, the imaging unit 7) and transmits image data to the PC 3 in accordance with various control instructions for the optical image acquiring unit 5 that are transmitted from the PC 3. As a recent example of the signal cable L2, a USB (universal serial bus) cable, etc., can be used, and with a USB cable, in addition to the sending and receiving of signals, power can be supplied to the X-ray imaging apparatus 2 as well.

The PC 3 sets various parameters (for example, sets the resolution) in and instructs X-ray imaging to the X-ray imaging apparatus 2 via the signal cable L2, takes in image data, expressing an X-ray image, from the X-ray imaging apparatus 2, performs various analysis (for example, extraction, magnification, etc., of a specific region of an image), and stores the image data and data expressing the analysis results in a memory. Furthermore, the PC 3 displays an X-ray image on the display 4 based on the image data taken in from the X-ray imaging apparatus 2 and displays the analysis results, etc., concerning the image data. Here, the display 4 has a display unit, such as a CRT (cathode ray tube), an LCD (liquid crystal display), etc.

Figure 3:
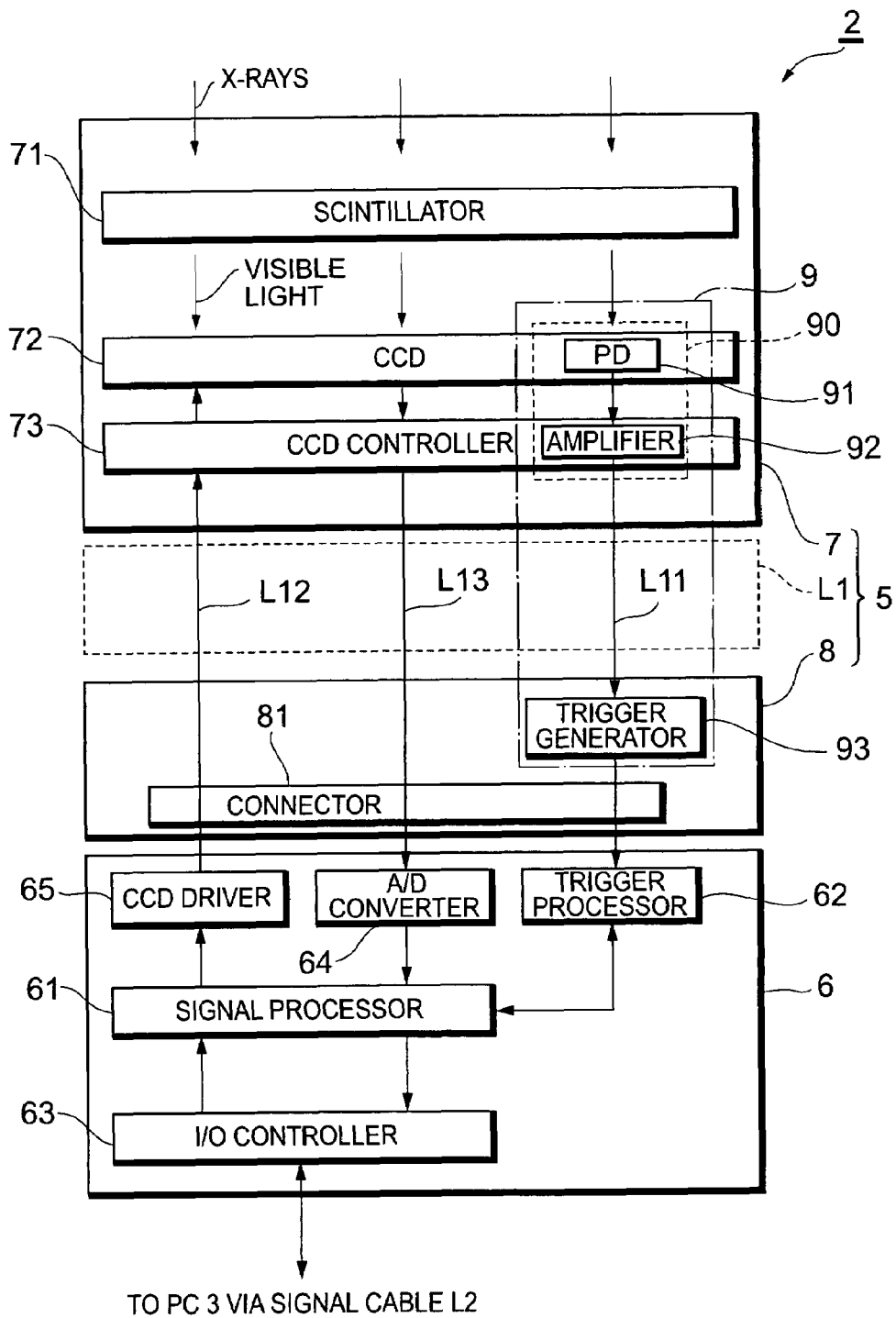
FIG. 3 is a block diagram of an arrangement of an X-ray imaging apparatus according to the embodiment.

An arrangement of the X-ray imaging apparatus 2 shall now be described in detail with reference to FIG. 3. The imaging unit 7 has a scintillator 71, a CCD 72, and a CCD controller 73. When X-rays are made incident thereon, the scintillator 71 emits visible light of a light amount corresponding to the energy amount of the X-rays. Upon illumination of the visible light from the scintillator 71, the CCD 72 performs photoelectric conversion of the visible light, generates charges corresponding to the light amount of the visible light (charges expressing an image), and accumulates the charges in a readable manner (this process shall also be referred to hereinafter as "imaging"). Upon receiving a controlling signal for the CCD 72 from the controlling unit 6, the CCD controller 73 drives and controls the CCD 72 in accordance with the controlling signal. Here, the controlling signal for the CCD 72 is, for example, an imaging instruction of an X-ray image, a read instruction, etc. In the description that follows, "signal" shall refer to an analog signal.

The connecting unit 8 is for detachably connecting the optical image acquiring unit 5 to the controlling unit 6 and has a connector 81. The connector 81 is, for example, a 36-pin MDR connector, etc. The controlling signal for the imaging unit 7 by the controlling unit 6 is transmitted from the controlling unit 6 to the imaging unit 7 via the connecting unit 8 and the signal cable L1 (controlling signal line L12). Image signals expressing the X-ray image taken by the imaging unit 7 are transmitted to the controlling unit 6 via the connecting unit 8 and the signal cable L1 (image signal line L13).

The optical image acquiring unit 5 has a trigger generating unit 9. The trigger generating unit 9 generates trigger signals for the imaging unit 7 that express an imaging start instruction and an imaging end instruction for an X-ray image and outputs these trigger signals to the controlling unit 6. The trigger generating unit 9 has an X-ray detecting unit 90 having a PD (photodiode) 91 and an amplifier 92, and a trigger generator 93 that is connected to the X-ray detecting unit 90 via the signal cable L1 (detection signal line L11).

The controlling unit 6 has a signal processor 61, a trigger processor 62, an I/O controller 63, an A/D converter 64, and a CCD driver 65. The controlling unit 6 has a connecting terminal, to and from which the connector 81 of the optical image acquiring unit 5 can be attached and detached, and the sending and receiving of various signals to and from the optical image acquiring unit 5 are performed via this connecting terminal. The controlling unit 6 also performs the sending and receiving of various data to and from the PC 3 via the signal cable L2. In the description that follows, "data" shall refer to digital data.

In accordance with trigger data (data indicating an imaging start timing and an imaging end timing for an X-ray image), which shall be described below and are input from the trigger processor 62, and command data, which are input from the PC 3 via the I/O controller 63, the signal processor 61 generates control data for the optical image acquiring unit 5 (or the trigger processor 62 or other component) or takes in image data from the optical image acquiring unit 5 via the A/D converter 64 and transmits the image data via the I/O controller 63 to the PC 3 side.

As shall be described in detail below, if, after detecting a falling edge (start) timing of a below-described trigger signal pulse (a Low signal pulse P4 or P8 of a trigger signal S6, shown in FIG. 5) input from the trigger generating unit 9 (that is, upon detecting a start timing of an entire X-ray irradiation period T1, shown in FIG. 5), a rising edge (end) of the pulse does not occur within an elapse, from the falling edge timing, of a period slightly longer than a pulse width (pulse width W, shown in FIG. 5) of a pulse generated by a monostable multivibrator 93b, the trigger processor 62 outputs, at the timing of elapse, the trigger data, indicating the imaging start timing, to the signal processor 61. Thus, even if a single isolated signal of short pulse width that is due to noise is input into the trigger processor 62, a malfunction, in which the trigger data indicating the imaging start timing is output erroneously, can be avoided. Furthermore, upon detecting a rising edge timing of the trigger signal pulse input from the trigger generating unit 9 (an end timing of the entire X-ray irradiation period T1, shown in FIG. 5), the trigger processor 62 outputs, at the rising edge timing, the trigger data, indicating the imaging end timing, to the signal processor 61.

The I/O controller 63 has an interface for performing the sending and receiving of data to and from the PC 3 via the signal cable L2 based on a data transmission method such as USB, IEEE 1394, etc. The I/O controller 63 is not restricted to wired data transmission and may instead have an interface corresponding to a wireless data transmission method, such as wireless LAN (local area network), Bluetooth, etc.

The A/D converter 64 converts image signals taken in from the imaging unit 7 into image data and outputs the data to the signal processor 61. The CCD driver 65 generates controlling signals (signal pulses) according to various control data for the optical image acquiring unit 5 that are input from the signal processor 61 and outputs the controlling signals to the optical image acquiring unit 5.

The above-described functions of the signal processor 61 may be realized by hardware or may be realized by software.

Figure 4:
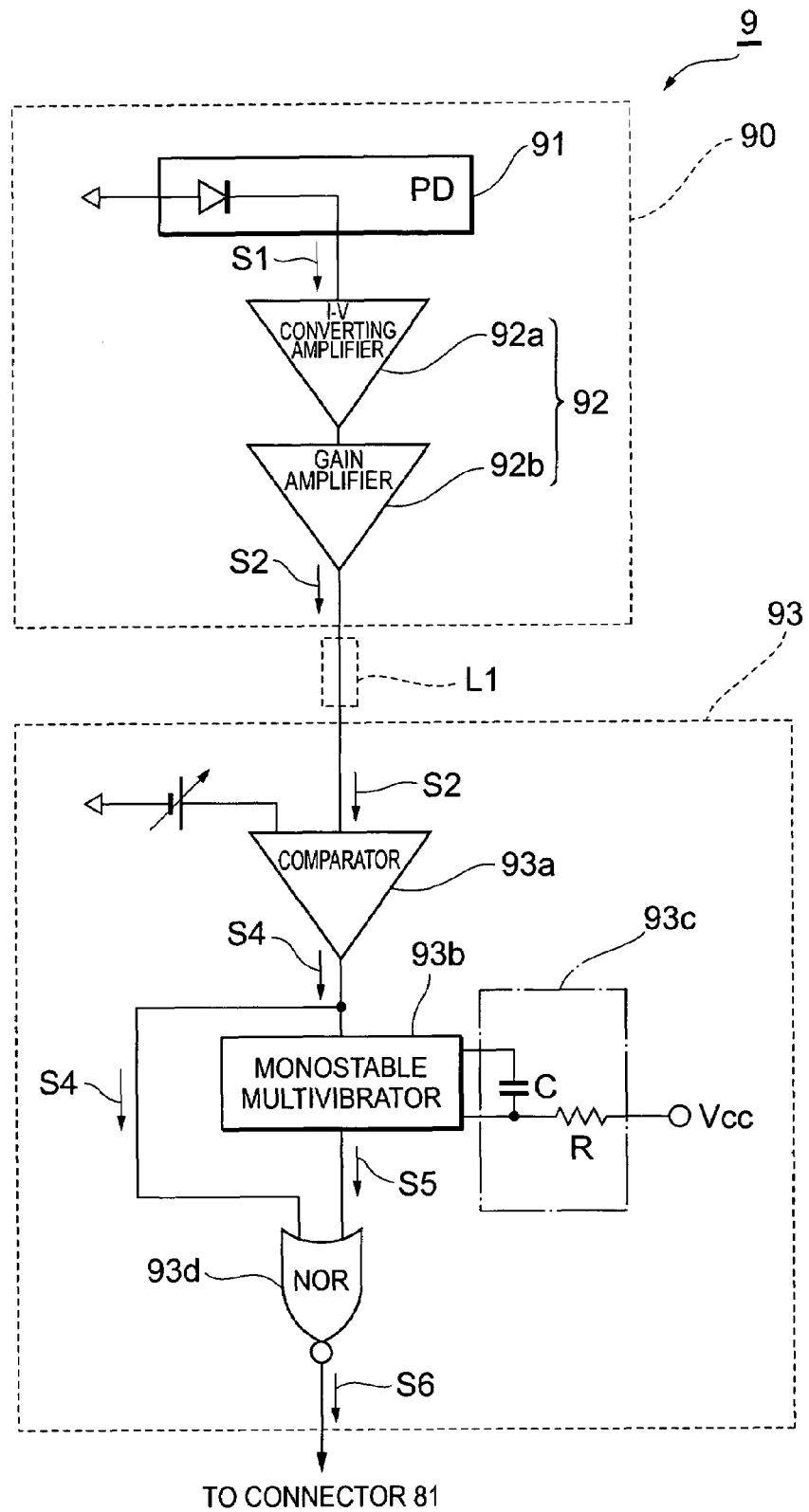
FIG. 4 is a block diagram of an arrangement of a trigger generating unit of the embodiment.

An arrangement and operation of the trigger generating unit 9 shall now be described in detail with reference to FIGS. 4 and 5.

The PD 91 detects X-rays irradiated by the X-ray irradiating apparatus 1. Here, the X-ray irradiation is stationary in accordance with the voltage waveform of the complete DC voltage obtained by the high-frequency inverter method in the X-ray irradiating apparatus 1. The PD 91 outputs an electrical signal (referred to hereinafter as "signal S1") in accordance with the energy amount of the detected X-rays. The signal S1 thus contains a pulse P1 with a pulse width corresponding to the entire X-ray irradiation period T1 (approximately a few dozen msec to few seconds).

The amplifier 92 has an I-V converting amplifier 92a and a gain amplifier 92b. At the amplifier 92, the I-V converting amplifier 92a converts the signal S1, input from the PD 91, from a current value to a voltage value, and further the gain amplifier 92b amplifies the signal S1, which has been converted to the voltage value, to a signal level enabling processing by the connecting unit 8 at the subsequent stage and outputs the amplified signal as a signal S2 (X-ray detection signal). The amplifier 92 outputs the signal S2 to the trigger generator 93 via the signal cable L1 (detection signal line L11).

The trigger generator 93 has a comparator 93a, the monostable multivibrator 93b, a time-constant-determining C, R connection 93c (first pulse output unit), and a NOR circuit 93d (second pulse output unit).

When the signal S2, input from the amplifier 92 via the signal cable L1 (detection signal line L11), is no less than a reference signal level S3, the comparator 93a outputs a signal S4 to the monostable multivibrator 93b and the NOR circuit 93d. The signal S4 contains a pulse P2 with a pulse width corresponding to a time width during which the signal S2 is no less than the reference signal level S3 (time width substantially equal to the entire X-ray irradiation period T1).

When the signal S4 from the comparator 93a is input, the monostable multivibrator 93b outputs, in synchronization with the rising edge (start) of the pulse P2, contained in the signal S4, a pulse P3 (signal S5) to the NOR circuit 93d. Here, the pulse P3 (first pulse) has a pulse width W (20 to 40 msec) that is determined by the respective values of a capacitance C and a resistance R, included in the time-constant-determining C, R connection 93c.

If the pulse P3 is contained in the signal S5 or the pulse P2 is contained in the signal S4, the NOR circuit 93d outputs a Low signal during a period in which either state continues, and in the other case, that is, if the pulse P3 is not contained in the signal S5 and the pulse P2 is not contained in the signal S4, the NOR circuit 93d outputs a High signal during a period in which this state continues.

The NOR circuit 93d thus outputs the trigger signal S6 that contains the Low signal pulse P4 (second pulse), with a pulse width corresponding to the entire X-ray irradiation period T1, during the entire X-ray irradiation period T1.

For cyclic X-ray irradiation in accordance with a half-wave rectified waveform of an AC power supply voltage, the X-ray imaging apparatus 2 can output the same trigger signal S6 as that in the above-described case of stationary X-ray irradiation. An operation, in which the trigger generating unit 9 outputs the trigger signal S6 when the X-ray irradiation by the X-ray irradiating apparatus 1 is cyclic at a cycle of 50 Hz or 60 Hz in accordance with a half-wave rectified waveform of an AC power supply voltage, shall now be described.

Figure 5:
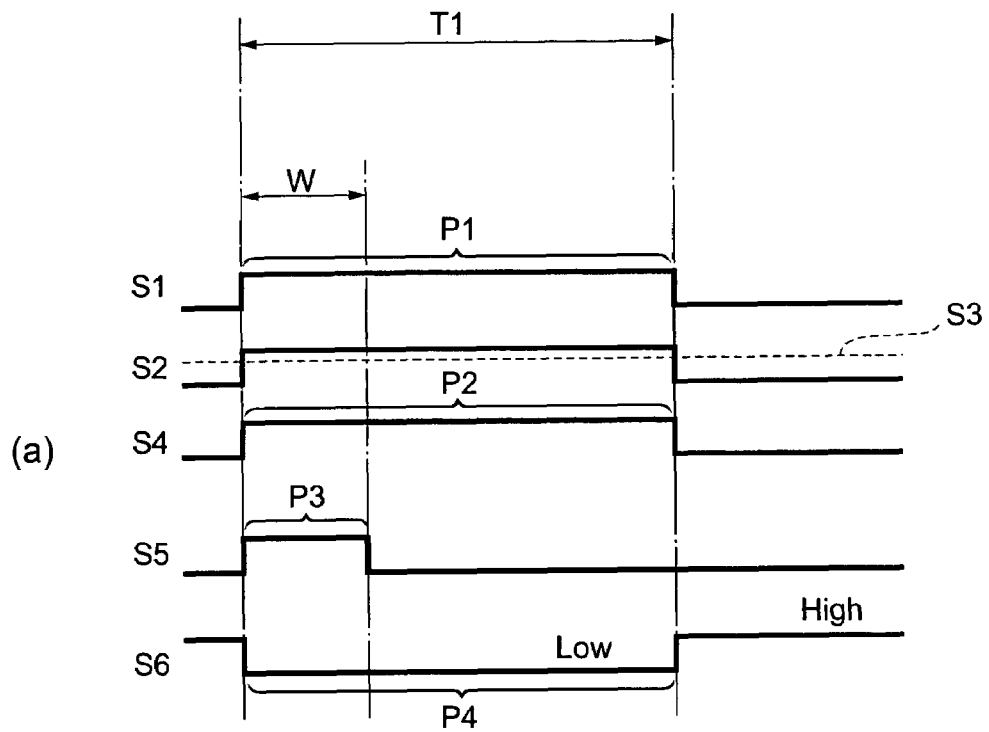
FIG. 5 shows timing charts for describing an operation of the trigger generating unit of the embodiment.
Figure 5:
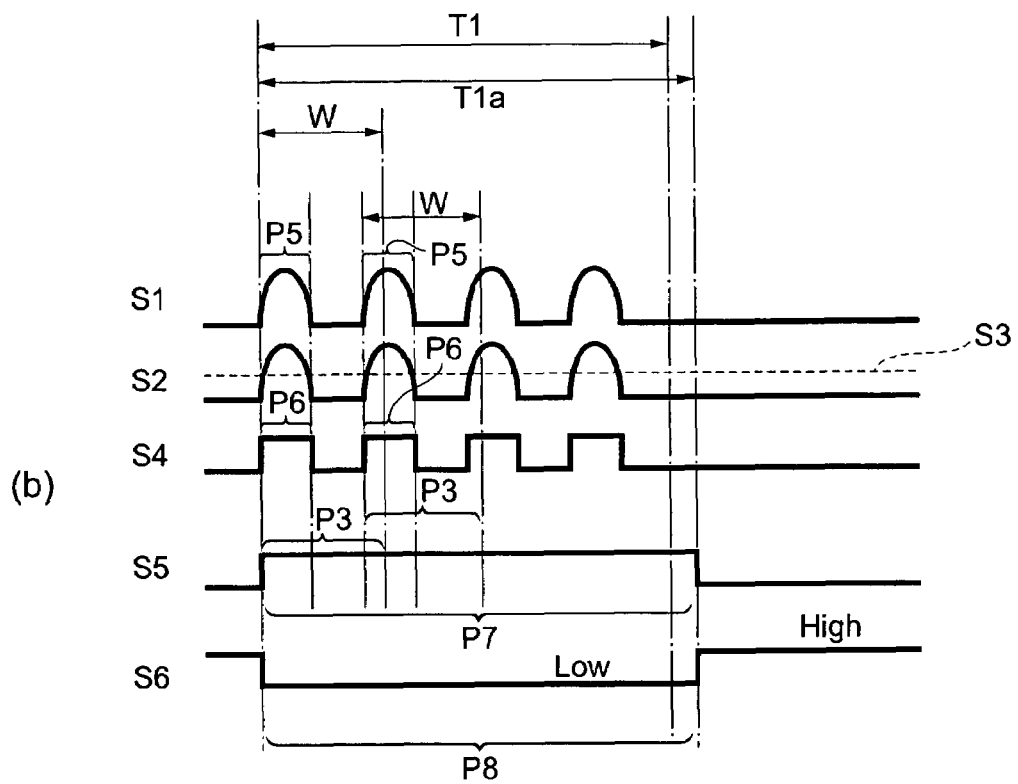

In this case, the signal S2 (and likewise the signal S1), input into the trigger generator 93 from the X-ray detecting unit 90, contains a plurality of pulses P5 in a cyclic manner as shown in (b) in FIG. 5. The signal S4 also contains a plurality of pulses P6 in a cyclic manner in accordance with the pulses P5 (signals S1 and S2).

When a pulse P6 is input, the monostable multivibrator 93b outputs the pulse P3 with the pulse width W. When during this output of the pulse P3, a pulse P6 is input anew, the monostable multivibrator 93b outputs the pulse P3 anew in synchronization with the rising edge (start) of the newly input pulse P6. Thus, at the monostable multivibrator 93b, as long as the pulse P6 is input during the output of the pulse P3, the pulse width of the signal S5 continues to be extended beyond the pulse width W of the pulse P3. A pulse P7 (signal S5), having a pulse width T1a that is slightly longer than a period (entire X-ray irradiation period T1), in which the signal S1 contains the pulses P5 in a cyclic and continuous manner, is thereby output.

Here, if the pulse P7 is contained in the signal S5 or the pulse P6 is contained in the signal S4, the NOR circuit 93d outputs a Low signal during a period in which either state continues, and in the other case, that is if the pulse P7 is not contained in the signal S5 and the pulse P6 is not contained in the signal S4, the NOR circuit 93d outputs a High signal during a period in which this state continues.

The NOR circuit 93d thus outputs the trigger signal S6 that contains the Low signal pulse P8, with the pulse width T1a substantially corresponding to the entire X-ray irradiation period T1, during the entire X-ray irradiation period T1.

Thus, regardless of whether the X-ray irradiation by the X-ray irradiating apparatus 1 takes on the form of a stationary pulse of wide width in accordance with the voltage waveform of the complete DC voltage obtained by the high-frequency inverter method in the X-ray irradiating apparatus 1 or takes on the form of cyclic pulses of narrow width in accordance with the half-wave rectified waveform of the AC power supply voltage, the trigger generating unit 9 outputs the trigger signal S6 that contains the Low signal pulse P4 or P8 with a pulse width corresponding to the entire X-ray radiating period T1 in likewise manner in both cases.

An operation of the X-ray imaging apparatus shall now be described with reference to FIG. 6. Upon input of the trigger signal S6 from the trigger generating unit 9, the trigger processor 62 outputs, to the signal processor 61, the trigger data that indicates the imaging start timing for the X-ray image and the trigger data that indicates the imaging end timing.

If upon detecting the falling edge (start) timing of the Low signal pulse P4 (or P8), the rising edge of the Low signal pulse P4 does not occur until an elapse, from the falling edge timing, of a period slightly longer than the pulse width W, the trigger processor 62 outputs, at the timing of elapse, the trigger data, indicating the imaging start timing, to the signal processor 61. A malfunction, in which the trigger data indicating the imaging start timing is output erroneously due to noise, can thereby be avoided.

Figure 6:
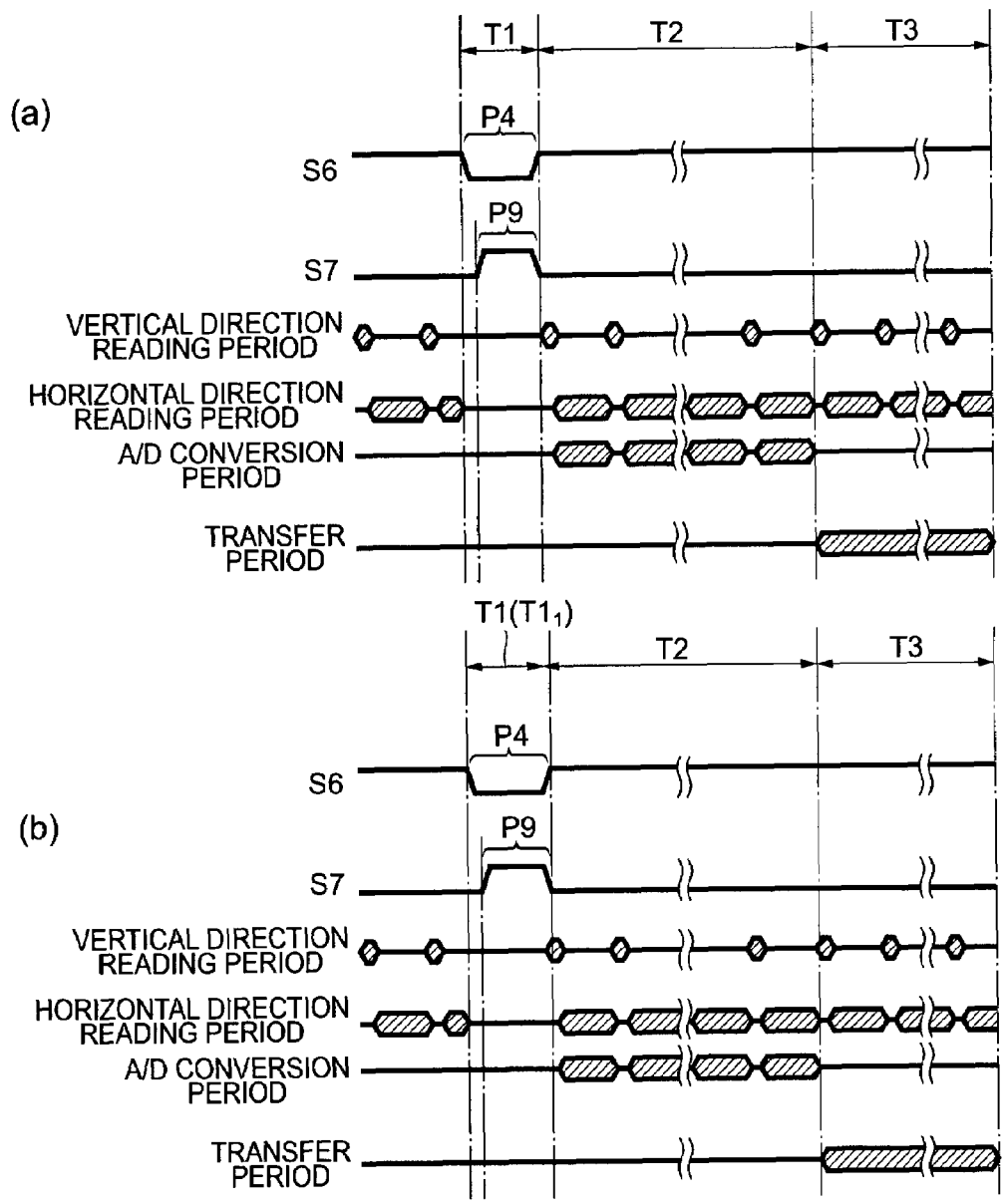
FIG. 6 shows timing charts for describing an operation of the X-ray imaging apparatus according to the embodiment.

Then upon actually detecting the rising edge (end) timing of the Low signal pulse P4 (or P8), the trigger processor 62 outputs the trigger data indicating the imaging end timing to the signal processor 61 at the rising edge timing as shown in (a) in FIG. 6 (first imaging mode).

The signal processor 61 may, as shown in (b) in FIG. 6, output the trigger data indicating the imaging end timing to the signal processor 61 at a timing at which a predetermined period $T1_1$ (a period that is preset in correspondence to the entire X-ray irradiation period T1) just elapses from the falling edge (start) timing of the Low pulse P4 (second imaging mode).

Based on command data transmitted from the PC 3 via the signal processor 61, the trigger processor 62 sets in which of the first and second imaging modes the X-ray imaging is to be performed. The imaging end timing in the second imaging mode may be arranged to be detected not by the trigger processor 62 but by the signal processor 61 instead.

The signal processor 61 makes the CCD driver 65 output, to the imaging unit 7, a pulse P9 (controlling signal S7) with a pulse width corresponding to a period from the input of the trigger data indicating the imaging start timing to the input of the trigger data indicating the imaging end timing under the first imaging mode (or the period until the imaging end timing under the second imaging mode).

Here, the rising edge (start) timing of the pulse P9 is delayed from the start timing of the entire X-ray irradiation period T1 by a period that slightly exceeds the pulse width W. This is because, as described above, in order to prevent malfunctions due to noise, the output of the trigger data indicating the imaging start timing at the trigger processor 62 is delayed from the start timing of the entire X-ray irradiation period T1. The imaging unit 7 then starts imaging (accumulation of image signals) in synchronization with the rising edge (start)

timing of the pulse P9 and ends imaging (accumulation of image signals) in synchronization with the falling edge (end) timing of the pulse P9 (period T1).

Then after the end of imaging, the image signals accumulated by the imaging unit 7 during the imaging period are read by the signal processor 61 (period T2). Here, the signal processor 61 makes the CCD controller 73 of the imaging unit 7 read horizontal component and vertical component image signals alternately from the CCD 72 in accordance with the resolution designated by the PC 3, etc., in advance. The image signals read from the imaging unit 7 are successively converted into image data at the A/D converter 64 and are taken into the signal processor 61.

After the period T2, the signal processor 61 successively transfers the image data, taken in via the A/D converter 64, to the PC 3 via the I/O controller 63 (period T3).

As described above, with the X-ray imaging apparatus 2 according to the present embodiment, regardless of whether the X-ray irradiation by the X-ray irradiating apparatus 1 takes on the form of a stationary pulse of wide width in accordance with the voltage waveform of a complete DC voltage obtained by the high-frequency inverter method in the X-ray irradiating apparatus 1 or takes on the form of cyclic pulses of narrow width in accordance with the half-wave rectified waveform of the AC power supply voltage, the trigger indicating the imaging start timing for an X-ray image and the trigger indicating the imaging end timing can be output appropriately while preventing malfunctions in the imaging operation due to noise in likewise manner in both cases. Taking of a good X-ray image is thereby enabled.

Furthermore, the detection signal line L11 that transmits the signal S2 for generating the trigger indicating the imaging start timing (and furthermore, a controlling signal line L12, the image signal line L13, and the GND line L14) are disposed at the inner, central portion of the signal cable L1, and the controlling signal lines L12 are disposed at the outer side thereof. Thus, even when an impact, due to collision, due to dropping, etc., or due to sudden bending, etc., is applied to the signal cable L1 itself, such an impact can be adequately relaxed, with respect to the detection signal line L11 that is securely disposed at the inner, central portion of the signal cable L1 (in particular, disposed inside the holding member 12), by the presence of the controlling signal lines L12 that are disposed at the outer side of the detection signal line L11. Thus, even when an impact is applied to the signal cable L1, generation of noise due to the impact is unlikely to occur in the detection signal line L11. Malfunctions in the imaging operation, in which noise is generated in the detection signal line L11 and a trigger indicating the imaging start timing is thereby generated erroneously, can thus be suppressed reliably.

The present invention is not restricted to the above-described embodiment, and various modifications are possible. For example, although with the present embodiment, the trigger generator 93 is disposed in the connecting unit 8, the present invention is not restricted thereto, and the trigger generator 93 may instead be disposed in the controlling unit 6. In this case, the signal S2 output from the X-ray detecting unit 90 (amplifier 92) is input, via the signal cable L1 and the connector 81 of the connecting unit 8, into the trigger generator 93, disposed inside the controlling unit 6.

The X-ray imaging apparatus according to the above-described embodiment has an arrangement that includes: the imaging unit, taking an X-ray image obtained by X-ray irradiation; the X-ray detecting unit, outputting, when X-rays are irradiated, the X-ray detection signal over the irradiation period; the first pulse output unit, outputting, when the X-ray detection signal is input from the X-ray detecting unit, the first pulse with the preset pulse width at the input timing of the X-ray detection signal and, when a new X-ray detection signal is input from the X-ray detecting unit during output of the first pulse, extendingly outputting the first pulse, being output, further for just the period corresponding to the pulse width from the input timing of the new X-ray detection signal; the second pulse output unit, outputting, in a state where one or both of the X-ray detection signal and the first pulse are being input, the second pulse, with the pulse width corresponding to the period of input, at the start timing of the input period; and the controlling unit, controlling, when the second pulse is input, the imaging unit to start imaging based on the start timing of the second pulse.

Also, with the present X-ray imaging apparatus, the controlling unit preferably controls the imaging unit to end imaging based on the end timing of the second pulse. By thus ending imaging based on the end timing of the second pulse, imaging is ended accurately in accordance with the end timing of the entire X-ray irradiation period.

Also, preferably with the present X-ray imaging apparatus, when a preset period elapses from the start timing of the second pulse, the controlling unit controls the imaging unit to end imaging at the timing of elapse of this period. By forcibly ending imaging at the timing of elapse of the preset period from the start timing of the second period, imaging is ended reliably. An unexpected situation, such as an inability to end imaging due to a malfunction caused by noise or ending of imaging before expiration of an appropriate imaging period, etc., can thereby be avoided.

INDUSTRIAL APPLICABILITY

The apparatus of the present invention can be used as an X-ray imaging apparatus that can appropriately detect an imaging start timing and can take a good X-ray image while preventing malfunctions due to noise regardless of whether the X-ray irradiation is cyclic in accordance with a waveform resulting from half-wave rectification of an AC power supply voltage or is stationary in accordance with a voltage waveform of a complete DC voltage obtained by a high-frequency inverter method.

The invention claimed is:

1. An X-ray imaging apparatus comprising:
    an imaging unit, taking an X-ray image obtained by X-ray irradiation;
    an X-ray detecting unit, outputting, when X-rays are irradiated, an X-ray detection signal over an irradiation period;
    a first pulse output unit, outputting, when the X-ray detection signal is input from the X-ray detecting unit, a first pulse with a preset pulse width at an input timing of the X-ray detection signal and, when a new X-ray detection signal is input from the X-ray detecting unit during output of the first pulse, extendingly outputting the first pulse, being output, further for a period corresponding to the pulse width from the input timing of the new X-ray detection signal;
    a second pulse output unit, outputting, in a state where one or both of the X-ray detection signal and the first pulse are being input, a second pulse, with a pulse width corresponding to a period of the input, at a start timing of the input period; and
    a controlling unit, controlling, when the second pulse is input, the imaging unit to start imaging based on a start timing of the second pulse.

2. The X-ray imaging apparatus according to claim 1, wherein the controlling unit controls the imaging unit to end imaging based on an end timing of the second pulse.

3. The X-ray imaging apparatus according to claim 1, wherein, when a preset period elapses from the start timing of the second pulse, the controlling unit controls the imaging unit to end imaging at a timing of elapse of this period.

* * * * *